United States Patent [19]

Okada

[11] 4,219,013
[45] Aug. 26, 1980

[54] FORWARD VIEWING ENDOSCOPE WITH SPECIFIC COVER FOR PHOTOGRAPHIC CASSETTE OPENING

[75] Inventor: Takeshi Okada, Hachioji, Japan

[73] Assignee: Olympus Optical Co., Ltd., Tokyo, Japan

[21] Appl. No.: 865,883

[22] Filed: Dec. 30, 1977

[30] Foreign Application Priority Data

Jan. 19, 1977 [JP] Japan .................. 52-5145[U]

[51] Int. Cl.² .............................................. A61B 1/04
[52] U.S. Cl. .......................................... 128/4; 128/6; 354/62; 354/275
[58] Field of Search ................................ 128/4–8; 354/62, 63, 275

[56] References Cited

U.S. PATENT DOCUMENTS

| 2,665,617 | 1/1954 | Marcouiller | 128/8 X |
| 2,959,089 | 11/1960 | Hett | 128/7 X |
| 3,329,074 | 7/1967 | Gosselin | 128/4 X |
| 3,426,633 | 2/1969 | Fox | 128/6 X |
| 3,523,496 | 8/1970 | Nerwin | 354/275 X |
| 3,608,547 | 9/1971 | Sato et al. | 128/6 |
| 3,980,078 | 9/1976 | Tominaga | 128/4 |
| 4,085,742 | 4/1978 | Okada | 128/6 X |

FOREIGN PATENT DOCUMENTS

| 67695 | 6/1940 | Czechoslovakia | 354/275 |
| 546369 | 7/1942 | United Kingdom | 128/7 |

*Primary Examiner*—Edgar S. Burr
*Assistant Examiner*—Steven A. Bratlie

[57] ABSTRACT

A forward viewing tape endoscope comprises a head body having a photographic optical system disposed at the forward end of the head body and a film cassette chamber provided behind the photographic optical system, an outer tube surrounding the head body and having an opening bored in the peripheral wall to effect communication between the film cassette chamber and outer tube, and a cover detachably mounted on the opening by a tightening device. The replacement of a film cassette is carried out without the insertion and withdrawal of the head body and the undesirable exposure of the photographic optical system to the atmosphere.

4 Claims, 5 Drawing Figures

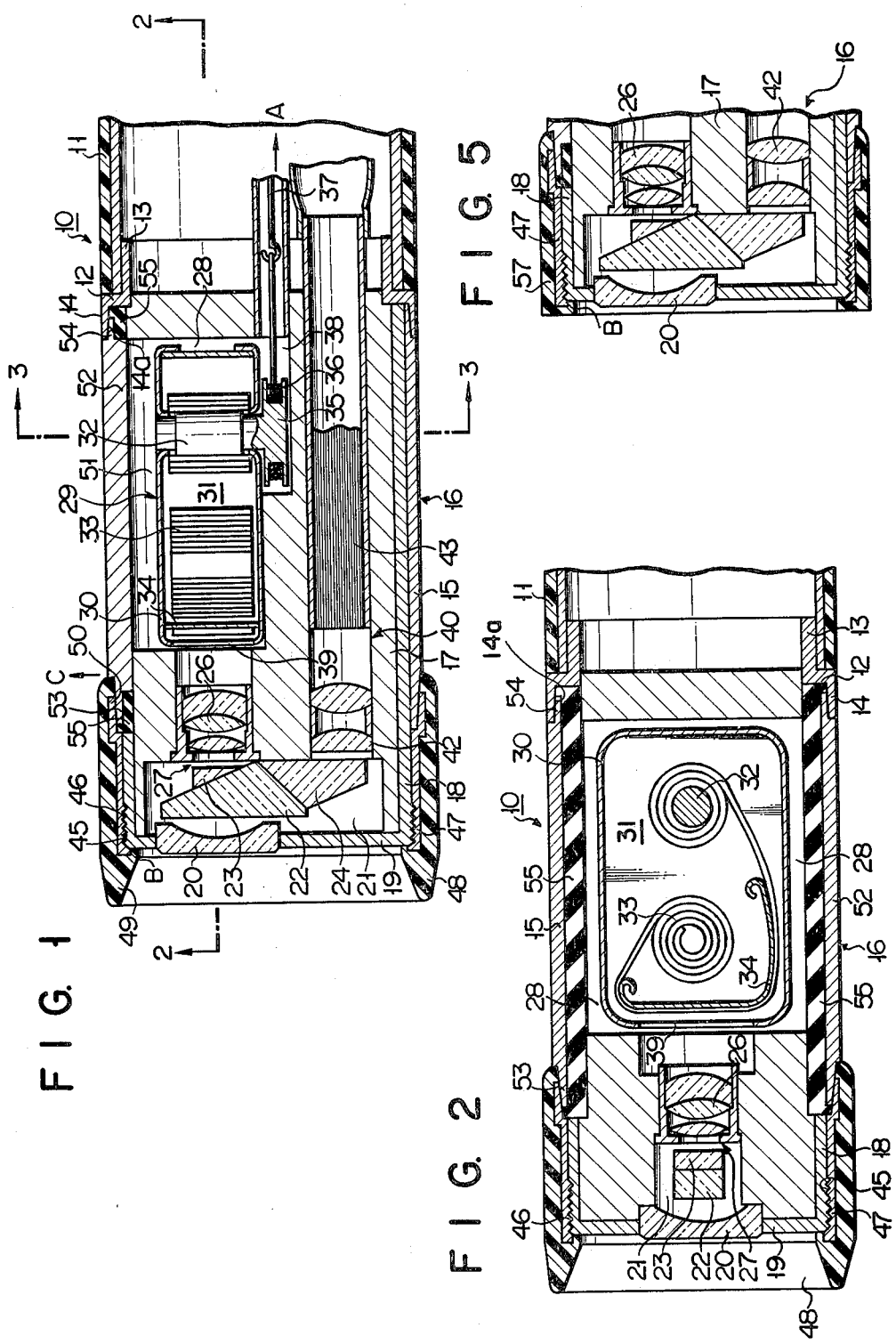

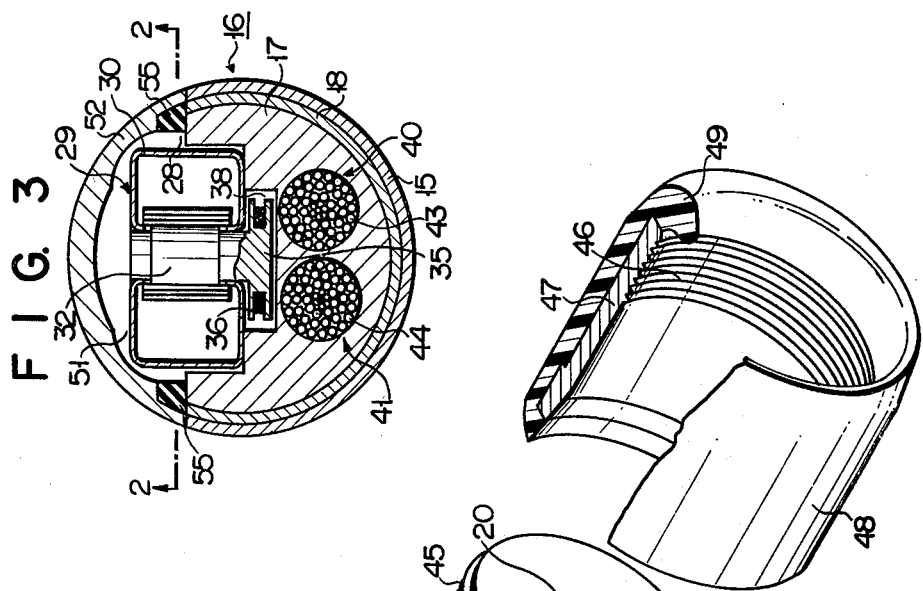
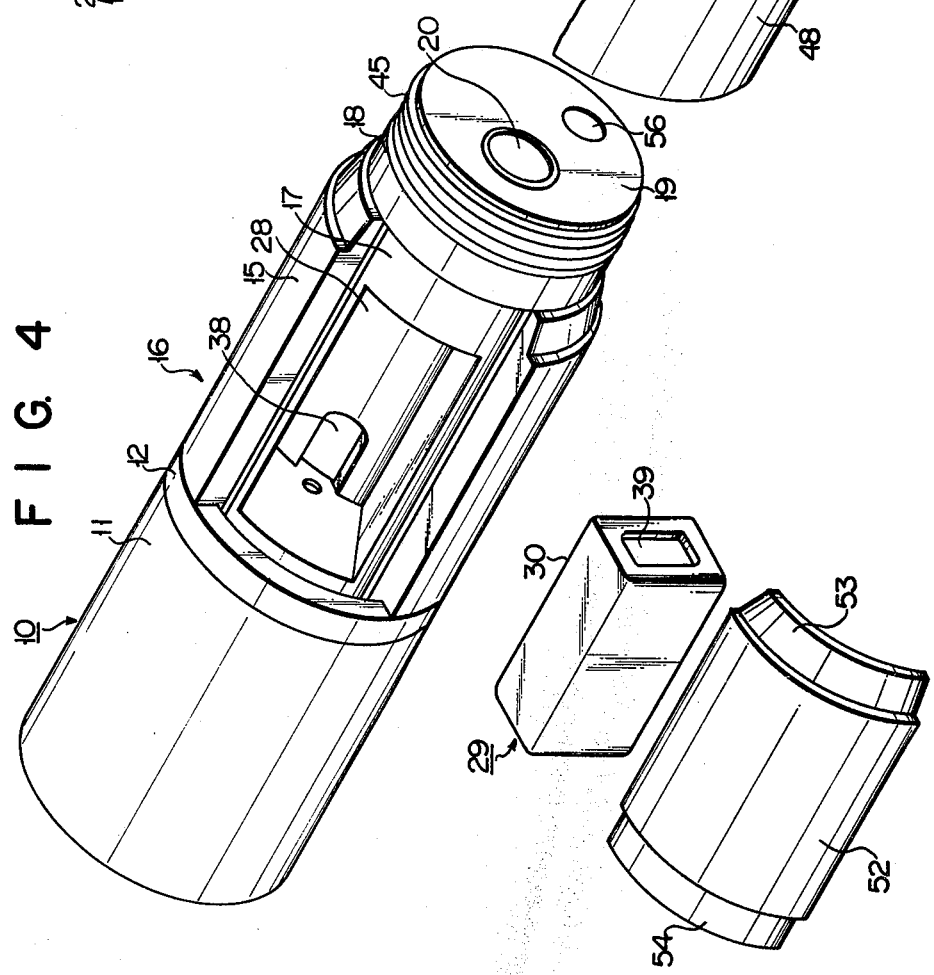

FORWARD VIEWING ENDOSCOPE WITH SPECIFIC COVER FOR PHOTOGRAPHIC CASSETTE OPENING

BACKGROUND OF THE INVENTION

1. Field of the Invention

This invention relates to a forward viewing type endoscope provided with coeliac photographic device.

2. Description of the Prior Art

With the conventional type of an endoscope having a built-in photographic device, for example, a gastrocamera, a head portion disposed at a distal end of a flexible tube section is loaded with a film cassette. A prescribed length of the film is taken up on a reel after each cycle of light exposure. A film feed shaft and a film takeup shaft are spatially received in the endoscope film cassette. A film path and a light-exposure section are provided between the two shafts. The film cassette is fitted into a cassette holder provided in the head body. Since an outer tube surrounds the head body, it is necessary to take the outer tube off the head body when the film cassette is inserted or pulled out, presenting difficulties in replacing a used film cassette by a fresh one. Further disadvantages of the prior art endoscope are that when the outer tube is taken off at the insertion or withdrawal of the film cassette, other mechanisms than the cassette holder such as a photographic optical system and an illumination optical system are unnecessarily exposed to the atmosphere with the possibility of these mechanisms being contaminated by deposition of, for example, dust.

SUMMARY OF THE INVENTION

It is accordingly an object of this invention to provide an forward viewing type endoscope whose head body has a film cassette chamber disposed behind a photographic optical system set at the forward end of the head body, thereby enabling a film cassette to be easily inserted or pulled out through the lateral wall of the head body.

Another object of the invention is to provide a forward viewing type endoscope which ensures the replacement of a used film cassette by a fresh one without exposing an optical system to the atmosphere.

Still another object of the invention is to provide a forward viewing type endoscope which prevents coeliac fluids from being carried into the head body.

According to this invention, there is provided a forward viewing type endoscope including a head portion comprising a head body, whose forward end is fitted with an optical system, and an outer tube surrounding the head body, which further comprises a film cassette chamber formed behind the optical system in the head body, a detachable cover mounted on the peripheral wall of the outer tube to close in liquid-tightness an opening for ensuring communication between the outer tube and film cassette chamber, and tightening means for securely setting the cover in position.

BRIEF DESCRIPTION OF THE DRAWING

FIG. 1 is a longitudinal sectional view of a distal end of a forward viewing type endoscope including a head portion according to one embodiment of this invention;

FIG. 2 is a sectional view on line 2—2 of FIG. 1;

FIG. 3 is a sectional view on line 3—3 of FIG. 1;

FIG. 4 is an exploded perspective view of the distal end portion of the forward viewing type endoscope of FIG. 1; and FIG. 5 is a longitudinal sectional view of the head portion of a forward viewing type endoscope according to another embodiment of the invention.

DETAILED DESCRIPTION OF THE PREFERRED EMBODIMENTS

Throughout the drawings, the same or similar parts are denoted by the same numerals. Referring to FIGS. 1 and 2, a forward viewing type endoscope generally denoted by reference numeral 10 has a flexible tube section 11. A connection ring 12 is formed of a cylindrical barrel 13 and a cylindrical engaging section 14 whose inner wall 14a takes a conical form. The barrel 13 of the connection ring 12 is inserted into the flexible tube section 11. The inner wall of the engaging section 14 is engaged by that peripheral surface of the rear end of an outer tube 15 of a head portion 16 which has a complementary shape to the inner wall. The head portion 16 is connected to the flexible tube section 11 by the connection ring 12. The outer tube 15 protects the head portion 16.

Referring to FIGS. 1 to 3, the head portion 16 comprises a substantially solid cylindrical head body 17, an intermediate tube 18 into the forward end wall of which the head body 17 is inserted, and the outer tube 15 surrounding the intermediate tube 18. A lens system 20 is provided in the forward end wall 19. Prisms 22, 23, 24 are received in an optical system chamber 21 formed in the forward end of the head body 17 in adjacent relationship with the lens system 20.

A lens system 26 whose optical axis coincides with that of the lens system 20 is disposed behind the prism 23. The lens system 26 constitutes a photographic optical system 27 together with the lens system 20 and prisms 22, 23. A depression constituting a film cassette chamber 28 is formed in the head body 17 to be positioned behind the lens system 26. A film cassette 29 fitted into the film cassette chamber 28 comprises a box-shaped casing 30 made of plastic material, a chamber 31 defined in the casing 30 and a film takeup shaft 32 disposed in the rear part of the chamber 31. Before photographing is carried out, an unexposed rolled film 33 is disposed in the forward part of the chamber 31 with its unrolled portion guided by a film guide member 34 concurrently acting as a film holder. The leading end of the unexposed film 33 is connected to the film takeup shaft 32. That end of the film takeup shaft 32 which projects out of the casing 30 is fitted with a reel 35. A film feed wire 36 is wound about the reel 35. One end of a control wire 37 is coupled to the free end end of the film feed wire 36. When the control wire 37 is manually pulled in a direction shown by the arrow A, the frames of the film are forwarded one after another. The reel 35 is received in another depression 38 formed in the head body 17 in adjacent relationship with the film cassette chamber 28.

The front wall of the casing 30 of the film cassette 29 is bored with a light exposure opening 39. An image of a foreground subject passing through the photographic optical system 27 is conducted through the light exposure opening 39 to be projected on a film 33 facing the light exposure opening 39. The head body 17 has an observation optical system 40 and an illumination optical system 41 disposed in parallel with the photographic lens 26 and film cassette chamber 27 (FIG. 3).

As seen from FIGS. 1 and 3, the observation optical system 40 comprises a lens system 42 and an observation optical fiberous bundle 43 disposed behind the lens system 42 and extending lengthwise of the head body 17. The illumination optical system 41 lies behind the observation optical system 40 as viewed from FIG. 1, and has the same construction as the observation optical system 40, though not shown in FIG. 1. An illumination optical fibrous bundle 44 is indicated in FIG. 3.

Referring to FIGS. 1 and 4, a male screw 45 is formed on the peripheral surface of the forward end portion of the intermediate tube 18. The male screw 45 is threadedly engaged with a female screw 46 formed in the inner wall of the forward end portion of a tightening member 47 surrounded with a soft and flexible protective member 48 made of plastic material. The forward end portion of the protective member 48 projects lengthwise from the front end wall 19 of the intermediate tube 18 and swells radially inward to constitute a seal section 49. The elastic deformation of the protective member 48 effects sealing of a junction B between the intermediate tube 18 and tightening member 47. With the foregoing embodiment, the soft and flexible forward end portion of the protective member 48 plays the double role of allowing the endoscope 10 to be inserted into the body cavity without any damage thereto and also acting as a hood. The rear end of the tightening member 47 is provided with an engagement section 50 whose inner wall takes a conical shape. An opening 51 communicating with the film cassette chamber 28 for insertion of the film cassette 29 thereinto is bored in that portion of the outer tube 15 which extends between the connection ring 12 and tightening member 47. The opening 51 is closed with a detachable cover 52 whose cross section has the same curvature as that of the head body 17. The forward and rear ends of the cover 52 are provided with engagement sections 53, 54 having a conical outer surface complementary to the inner conical surfaces of the engagement sections 50, 14 of the tightening member 47 and connection ring 12 respectively. The peripheral edge of the cover 52 is fitted with a soft and elastic packing 55 made of, for example, rubber. When the cover 52 thus constructed is mounted on the opening 51, liquid-tight sealing is ensured by the packing 55 between the peripheral edge of the cover 52 and opening 51. The conical outer surfaces of the engagement sections 53, 54 are closely fitted with the inner conical surfaces of the engagement sections 50, 14.

A forward viewing type endoscope constructed as described above is inserted into the body cavity with the head portion kept ahead. The interior of the body cavity is illuminated through the illumination optical system 41 by a flux of light rays supplied from a light source (not shown) disposed outside of the endoscope through the optical fibrous bundle 44, thereby effecting coeliac observation and photographing. Where a picture is to be taken of any diseased portion within the body cavity, said photographing is carried out by emitting, for example, a flash from the control section of the endoscope and projecting the flash on the interior of the body cavity through the optical fibrous bundle 44, illumination optical system 41 and illumination window 56 (FIG. 4), and at the same time actuating a photographic lever (not shown). An unexposed frame of the film 33 facing the light exposure opening 39 is exposed to light. When the control wire 37 is pulled at the control section of the endoscope, the reel 35 is rotated by means of the film feed wire 36, thereby causing the light-exposed frame of the film 33 to be taken up on the film takeup shaft 32 and also the succeeding unexposed frame of the film 33 to be conducted to the light exposure opening 39.

Where the film cassette 29 is taken out after a prescribed number of film frames have been photographed, the head portion 16 is first pulled out of the body cavity through the flexible tube section 11 of the endoscope 10. The protective member 48 is so rotated as to disengage the female screw 46 of the tightening member 47 from the male screw 45 of the intermediate tube 18. At this time, the protective member 48, together with the tightening member 47, is slowly shifted in the direction in which both members 47, 48 tend to be withdrawn from the forward end of the head portion 16. When the tightening member 47 is brought to the prescribed retarding position, the engagement section 50 is released from the engagement section 53 of the cover 52. The cover 52 is lifted outward at the engagement section 50 in a direction shown by the arrow C and pulled ahead of the head portion 16. The engagement section 54 of the cover 52 at the opposite end is drawn out of the engagement section 14 of the connection ring 12 to open the film cassette opening 51, enabling the film cassette 29 to be pulled out of the film cassette chamber 28 through the opening 51. At this time, the reel 35 integrally formed with the film cassette 29 is also taken out of the depression 38. The control wire 37 is pulled out by the film feed wire 36. Both wires 36, 37 can be separated from each other, by releasing their joints.

A fresh film cassette 29 is inserted into the film cassette chamber 28 through the film cassette opening 51. The free end of the film feed wire 36 wound about the reel 35 is coupled to the corresponding end of the control wire 37. The cover 52 is mounted on the film cassette opening 51 again. The rear engagement section 54 of the cover 52 is inserted into the engagement section 14 of the connection ring 12.

The lateral edge of the cover 52 is pressed against the peripheral edge of the film cassette opening 51. Where, under this condition, the protective member 48 is rotated in the opposite direction to that which is used in the removal of the film cassette 29, the protective member 48 and tightening member 47 are slowly transferred toward the rear end of the head portion 16. As a result, the engagement section 50 of the tightening member 47 rides on the engagement member 53 of the cover 52. The cover 52 is pressed toward the connection ring 12, and also toward the head portion 16 by means of the packing 55. Eventually the film cassette opening 51 is sealed by the cover 52 in liquidtightness. The seal section 49 of the protective member 48 is more elastically deformed as the tightening member 47 is further moved and is tightly pressed against the junction B (FIG. 1) of the threadedly engaged male screw 45 and female screw 46, thereby sealing the junction B in liquidtightness.

When the endoscope is inserted into the body cavity, the junction B of the threadedly engaged male and female screws 45, 46 which takes the foremost position in the head portion 16 is subject to the influx of, for example, coeliac fluids. Unless, therefore, the junction B is sealed in liquidlightness, the coeliac fluids tend to be carried into the endoscope through the junction B, and eventually into the film cassette chamber 28. According to this invention, however, the junction B is sealed in liquidtightness by the seal section 49 of the protective member 48. This arrangement suppresses the occurrence of the above-mentioned undesirable event and saves the film cassette chamber 28 from the intrusion of coeliac fluids.

Where it is unnecessary to cause the protective member concurrently to act as a hood, it is possible, as shown by referential numeral 57 of FIG. 5, to allow the protective member simply to take such shape as covers the junction B of the threadedly engaged male and female screws 45, 46 of the intermediate tube 18 and tightening member 47.

What is claimed is:

1. A forward viewing type endoscope including a head portion which comprises:
   a head body having a forward end portion;
   an optical system provided in the head body;
   a film cassette chamber formed behind the optical system in the head body;
   an outer tube surrounding the head body;
   an opening formed in the outer tube in registration with the film cassette chamber for inserting the film cassette, and removing the film cassette from the film cassette chamber therethrough;
   a detachable cover having a shape substantially complementary to the opening and fitted in the opening;
   a packing disposed between the opening and the cover extending about the edges of the cover and the opening for effecting a liquid-tight seal between the outer tube and the cover; and tightening means provided on the forward end of the head portion for securely sealing the cover in position.

2. An endoscope according to claim 1, wherein said tightening means comprises a tightening member threadably engaging the forward end of the head portion and provided at one end thereof with an engagement section for engaging the corresponding end of the cover, and a connection ring connected to the rear end of the head portion and having an engagement section for engaging the other end of the cover.

3. An endoscope according to claim 2, wherein said engagement sections of said tightening member and connection ring each have a conical inner surface, and said ends of said cover each have a conical outer surface complementary to the respective conical inner surface of the engagement section of the tightening member and connection ring.

4. An endoscope according to claim 2, wherein the tightening member is provided with screw threads mating with screw threads on the forward end of the head portion to form a screw connection for securely sealing the cover in position and a protective member of a soft material is mounted on the tightening member overlapping and sealing said screw connection.

* * * * *